United States Patent [19]

Matsukura et al.

[11] 4,371,470

[45] Feb. 1, 1983

[54] METHOD FOR MANUFACTURING HIGH QUALITY FATTY ACID ESTERS

[75] Inventors: Tadaaki Matsukura, Yokohama; Yukio Nakagawa, Tokyo, both of Japan

[73] Assignee: Lion Corporation, Tokyo, Japan

[21] Appl. No.: 235,577

[22] Filed: Feb. 18, 1981

[30] Foreign Application Priority Data

Feb. 28, 1980 [JP] Japan ................. 55-24335

[51] Int. Cl.³ .................... C11C 3/02; C09F 5/08
[52] U.S. Cl. ................. 260/428; 260/410.9 R
[58] Field of Search ............ 260/410.9 E, 428

[56] References Cited

U.S. PATENT DOCUMENTS

| Re. 22,751 | 4/1946 | Trent | 260/410.9 E |
|---|---|---|---|
| 2,383,601 | 8/1945 | Inman | 260/410.9 E |
| 2,494,366 | 1/1950 | Sprules | 260/410.9 E |
| 2,719,858 | 10/1955 | Hill | 260/410.9 E |
| 3,895,042 | 7/1975 | Taylor | 260/428 |

*Primary Examiner*—John F. Niebling
*Attorney, Agent, or Firm*—Brisebois & Kruger

[57] ABSTRACT

The invention provides a novel and very efficient method for the preparation of a high-quality lower alkyl, e.g. methyl, ester of a fatty acid in respects of color and odor which is suitable for the manufacture of high-grade soaps even without further purification by salting-out considered indispensable in the prior art processes. The inventive method utilizes a natural oil or fat as the starting material which is subjected to a two-step transesterification with methyl alcohol into a methyl ester of the fatty acid, from which the trace amounts of the colored or chromogenic impurities are removed by admixing an adsorbent. The types of the adsorbent as well as the temperature and the time for the adsorption are important for the effective decolorization. Best results were obtained with a mixture of an activated clay and an active carbon in a specified weight proportion.

5 Claims, No Drawings

METHOD FOR MANUFACTURING HIGH QUALITY FATTY ACID ESTERS

BACKGROUND OF THE INVENTION

The present invention relates to a method for manufacturing high quality fatty acid esters of lower alcohols useful as a starting material for the preparation of soaps, higher alcohols and the like. More particularly, the present invention relates to a method for manufacturing high quality fatty acid esters which can be processed into high-grade soap products without undertaking the treatment of salting-out as a means for purification hitherto considered to be indispensable in preparing soaps from fatty acid esters.

Lower alkyl esters of fatty acids such as methyl esters are widely used as a base material for the preparation of soaps and as a starting material for the synthesis of higher alcohols and certain kinds of surface active agents. They are manufactured industrially by the transesterification reaction of a fatty acid glyceride, i.e. oil or fat, and a lower alcohol, e.g. methyl alcohol. The industrial products of the lower alkyl esters of fatty acids manufactured in the above mentioned process naturally contain considerable amounts of colored or chromogenic impurities originating from the crude oil or fat as the starting material. Therefore, it is a usual practice that the crude soaps made from the esters are subjected to further purification by the method of salting-out since otherwise the quality of the finished soap bars obtained therefrom is very low.

Notwithstanding the industrially established process in which purification of the crude soaps by salting-out is almost always undertaken, such a purification treatment is preferably to be avoided because the procedure of salting-out requires very burdensome steps and extremely long time for aging when practiced in an industrial scale.

Generally speaking, there are known several methods for the purification of an organic substance such as lower alkyl esters of fatty acids to remove the colored or chromogenic impurities contained therein. They are, for example, a method of treatment with an alkali, a method of rectification distillation and a method of adsorption. These methods are not free from their respective drawbacks or problems. That is, the first method of alkali treatment has low efficiency and the yield of the purified products is impractically low. The method of rectification distillation is defective due to the consumption of relatively large quantity of heat energy and the yield of the purified products in the adsorption method is low due to the large loss of the material as remaining on the adsorbents. Thus, no satisfactory methods have yet been proposed for the mass production of fatty acid esters of high purity.

SUMMARY OF THE INVENTION

It is therefore an object of the present invention to provide a novel and improved method for manufacturing high quality lower alkyl esters of fatty acids capable of being processed into soaps without further purification by salting-out of the crude soaps or other troublesome methods free from the above described problems in the prior art from raw oils or fats as the starting material.

The method of the invention for manufacturing a high quality lower alkyl ester of a fatty acid by the alcoholysis of a fatty acid glyceride, i.e. natural oil or fat, comprises the steps of (a) esterifying the fatty acid glyceride by a first alcoholysis reaction with a lower alcohol in the presence of an alkali catalyst to form a first crude esterification product and glycerine, (b) separating the glycerine from the first crude esterification product, (c) esterifying the first crude esterification product by a second alcoholysis reaction with the lower alcohol in the presence of an alkali catalyst to form a second esterification product containing the unreacted lower alcohol and glycerine as dissolved or dispersed therein, (d) admixing the second crude esterification product with water in an amount from 30% to 150% by weight based on the amount of the lower alcohol contained in the second crude esterification product, (e) subjecting the second crude esterification product admixed with water to phase separation into the aqueous layer and layer of the lower alkyl ester of fatty acid, (f) stripping the lower alkyl ester of fatty acid of the water and unreacted lower alcohol contained therein, (g) admixing the thus stripped lower alkyl ester of fatty acid with from 1 to 10% by weight of an adsorbent to effect decolorization, and (h) removing the adsorbent from the thus decolorized lower alkyl ester of fatty acid.

DETAILED DESCRIPTION OF THE PREFERRED EMBODIMENTS

The first alcoholysis reaction as the step (a) in the inventive method is conventional and need not be described in detail.

The fatty acid glyceride as the starting material of the inventive method may be any kind of naturally occurring vegetable-origin or animal-origin fats or oils including palm oil, palm kernel oil, cottonseed oil, coconut oil and soybean oil as the examples of the former class and beef tallow, lard and various kinds of fish oils as the examples of the latter class. The main ingredients of these fats or oils are glycerides of several kinds of fatty acids containing considerable amounts of impurities such as aldehyde compounds, phospholipid compounds and free fatty acids. They are used without any purification but may be subjected to partial purification prior to the alcoholysis reaction, if desired. In particular, it is sometimes recommendable that the free fatty acids mentioned above as a class of impurities are esterified in advance by a preliminary reaction with the lower alcohol to decrease the acid value of the glyceride so that the fatty acid glyceride used as the starting material of the inventive method contains small amounts of the lower alkyl esters which may be the identical compounds with the objective products.

The lower alcohol used in the first alcoholysis reaction of the fatty acid glyceride is an aliphatic alcohol having from 1 to 3 carbon atoms in a molecule exemplified by methyl alcohol, ethyl alcohol, 1-propyl alcohol and 2-propyl alcohol although the principle of the inventive method is not limited to these alcohols. Among the above named alcohols, methyl alcohol is the most widely used because of the largest demand for the methyl esters.

The alkali catalyst used in the first alcoholysis reaction is also conventional including hydroxides and alcoholates, e.g. methylates and ethylates, of sodium and potassium.

The procedure of the first alcoholysis reaction in the step (a) is carried out according to a known method, in which the fatty acid glyceride is admixed with a lower alcohol in an amount of 2 to 10 equivalents and an alkali catalyst in an amount of 0.1 to 1.0% by weight based on the fatty acid glyceride and the reaction mixture is heated at or near the boiling temperature of the lower alcohol for about 0.5 to 2 hours under agitation until the reaction has come to substantial termination by the establishment of equilibrium. A conversion of 90 to 97% is usually obtained to form a blend of the first crude esterification product and glycerine.

The next step is the separation of the above obtained first crude esterification product and the glycerine. This phase separation can be effected readily by merely standing the reaction mixture for 1 to 15 minutes at 40° to 70° C. so that no particular means for accelerating phase separation, such as centrifugal separation, is usually required.

The crude esterification product obtained in the step (a) above and separated in the step (b) from the glycerine is then subjected to the second alcoholysis reaction in the step (c). The lower alcohol used in the second alcoholysis reaction is usually the same one as in the first alcoholysis reaction and the reaction temperature is also in the same range. Thus, 100 parts by weight of the first crude esterification product is admixed with from 5 to 50 parts by weight or, preferably, from 8 to 20 parts by weight of the lower alcohol and from 0.2 to 0.5 part by weight of the alkali catalyst and the reaction is carried out under agitation for about 5 to 60 minutes. An overall conversion of 98% or more of the starting fatty acid glyceride is readily obtained to give the second crude esterification product blended with a small amount of glycerine as well as the unreacted alcohol. This blend of the second crude esterification product and the glycerine forms a stable dispersion and cannot be separated into the phases of the former and the latter even by prolonged standing as such.

The above obtained second crude esterification product containing the unreacted lower alcohol, impurities and glycerine is then admixed with water in an amount of 30 to 150% by weight or, preferably, up to 100% by weight based on the amount of the unreacted lower alcohol contained therein and stirred uniformly. The addition of water in a limited amount as above is very essential in the inventive method since smaller amounts of water than 30% by weight bring about difficulties and prolongation of time in the subsequent phase separation while larger amounts of water than 150% by weight produce a very stable emulsion hardly separable into phases.

The reaction mixture thus admixed with water is then kept standing at a temperature of 40° to 60° C. whereby phase separation takes place. Though dependent on the height of the liquid layer, the phase separation is complete usually within 15 minutes but it is optional to use a means to accelerate the phase separation such as centrifugal separation, if desired. The lower limit 40° C. of the temperature is recommended since the velocity of phase separation is decreased at below 40° C. due to the partial solidification of certain ingredients in the reaction mixture. The lower layer formed by the phase separation is the aqueous mixture containing the unreacted lower alcohol, glycerine and colored impurities while the upper layer is composed of the objective lower alkyl esters of fatty acids with considerably high quality, which is readily separated from the lower layer.

It should be noted that admixing of water to the first crude esterification product after separation of the glycerine is very detrimental to the purpose of impurity removal since emulsification of the reaction mixture takes place by the addition of water and the phase separation of the resultant emulsion is carried out with great difficulties with accumulation of large amounts of sludge-like substances in the interfacial layer between the upper and the lower layers leading to a considerable loss in the yield of the ester product.

The above obtained ester product has a considerably high quality with respect to the colored or chromogenic impurities and may be used as such without further purification when no particularly high quality of the final products is desired. However, even the trace amounts of the impurities should be removed when highest quality is desired.

According to the present invention, this final purification is performed as follows. Thus, the ester product obtained above is subjected to stripping of any volatile matter, mainly water and unreacted lower alcohol, at a temperature of 100° C. or below under reduced pressure until volatile matters no longer distil out. Thereafter, the ester product is admixed with an adsorbent and agitated for 5 to 90 minutes or, preferably, for 10 to 60 minutes at a temperature of 50° to 110° C., or preferably, 60° to 100° C. These conditions are essential for satisfactory adsorption of the trace amounts of the impurities.

Suitable adsorbent is an activated clay or a mixture of an activated clay and an active carbon. When a mixture of an activated clay and an active carbon is used, the weight ratio of the active carbon to the activated clay is in the range from 1:9 to 8:2 or, preferably, from 1:9 to 4:6. The adsorbent is added to the ester product in an amount of 1 to 10% by weight or, preferably, 1.5 to 5% by weight since no satisfactory decolorizing effect is obtained with smaller amounts of the adsorbent while an excessively large amount of the adsorbent is undesirable due to the increased loss of the ester product by the adsorption on the adsorbent leading to a decreased yield of the final product.

The thus decolorized ester product is then separated from the adsorbent by a suitable solid-liquid separation method which may be conventional as filtration or centrifuge.

The above described inventive method is very advantageous in obtaining a high-quality lower alkyl esters of fatty acids superior in color suitable as a starting material for the manufacture of high-grade soaps and higher alcohols without further purification. In particular, high-grade soaps can be manufactured with the ester product obtained by the inventive method without the purification by salting-out which hitherto has been considered indispensable when highest quality is desired in the final products. This advantage is very significant industrially by the great saving of labors and facilities along with shortened working time for the purification.

Following are the examples to illustrate the present invention in further detail. In the examples, the quality evaluation of the product was undertaken in the manner described below.

(1) Yellowness: determination was carried out with an integrating sphere-type HTR meter made by Nippon Seimitsu Kogaku Co., Model SEP-H-2.
(2) Color: organoleptic test was conducted by 10 panel testers to give the evaluation in 4 grades A, B, C and D in comparison with a conventional product as a reference. The criterion of each of the grades is as follows.

A: color clearly better than the reference product
B: approximately equivalent in color to the reference product
C: slightly inferior in color to the reference product
D: color clearly inferior to the reference product (3) Odor: organoleptic test was conducted by 20 panel testers to give the evaluation in 5 grades A, B, C, D and E with a conventional product as a reference. The criterion of each of the 5 grades is as follows. The products graded in A and B are suitable as a commercial product while the products graded in C, D and E are not suitable as a commercial product.

A: equivalent to or better than the reference product
B: slightly inferior to the reference product
C: apparently inferior to the reference product with unpleasant odor ascribable to the starting raw material
D: considerably inferior to the reference product
E: clearly inferior to the reference product with strong odor ascribable to the starting material (4) Light resistance: the soap composition taken in a transparent container with an open mouth was exposed for 10 days or longer in spring season on the roof of a building and the change of the color in time was recorded.

(5) Heat resistance: the soap composition was kept for 14 days in a thermostat at 45° C. and the change of the color in time was recorded.

EXAMPLE 1

(Experiments No. 1 to No. 15)

The starting fatty acid glyceride was a 8:2 by weight mixture of beef tallow and coconut oil of which the free fatty acids contained in small amounts had been converted by a conventional method to corresponding methyl esters in an amount of 0.5% by weight in all of the Experiments excepting No. 15. The acid value of this starting material was 2.0 or below. Into a glass flask of 3 liter capacity equipped with a stirrer were taken 1500 g of the starting fatty acid glyceride and 600 g of methyl alcohol and 5.1 g of sodium hydroxide were added thereto. The transesterification reaction was carried out by agitating the above mixture at 60° to 70° C. for 1 hour. The conversion of the fatty acid glyceride to the ester product was 96.5%.

The mixture was kept standing to be separated into the upper layer of the ester product (primary ester) and the lower layer mainly composed of glycerine. The primary ester taken by phase separation was admixed with 150 g of methyl alcohol and 3 g of sodium hydroxide and agitated at 60° to 70° C. for 30 minutes to effect the second esterification reaction. The overall conversion of the fatty acid glyceride in this second esterification reaction reached 99.1%. This ester product was admixed with 200 g of water and agitated for 10 minutes followed by standing and separation into the ester product (secondary ester) in the upper layer and the mixture of methyl alcohol, water and glycerine in the lower layer.

The primary and secondary ester products were subjected to topping treatment at 60° to 70° C. for 1 hour under a pressure of 50 mmHg to be freed from trace amounts of water and methyl alcohol followed by admixing with a 9:1 by weight mixture of an activated clay and an active carbon as the adsorbent in an amount as indicated in Table 1 below and agitation at 80° C. for 30 minutes. The adsorbent was removed by filtration from the decolorized ester product.

Each 1300 g portion of the ester products obtained in varied purification conditions was taken in a kneader of 5 liter capacity with addition of a 30% by weight aqueous solution of sodium hydroxide in an amount of 1.03 times of the stoichiometric amount and saponified by agitating at 90° to 100° C. for about 120 minutes. In some of the experiments, the saponified product was further purified by salting-out by use of sodium chloride as the electrolyte with controlled water content followed by centrifugal separation into neat and nigre. The hydrosulfite was added to the saponified paste in an amount of 0.04% by weight based on the paste when salting-out was not undertaken or to the mixture under salting-out.

The thus obtained saponified paste or the salted-out neat soap was taken in a plastic vat and the water content thereof was reduced to 10 to 15% by evaporation in a hot air oven into respective soap chips without or with salting-out. The soap chips were admixed and blended with 1.0% by weight of a perfume and 0.3% by weight of titanium dioxide in a mixer and then milled and plodded by use of a laboratory-size three-roll mill and plodder followed by stamping with a pedalled stamping machine into a test soap composition. Table 1 below gives the results of the evaluation of 15 test soap compositions in color and odor.

TABLE 1

| Experiment No. | Ester product, primary (P) or secondary (S) | Adsorbent taken, % by weight | Salting-out | Color of Soap Yellowness | Color of Soap Organoleptic test | Odor, organoleptic test |
|---|---|---|---|---|---|---|
| 1 | P | — | Yes | 0.065 | — | — |
| 2 | P | — | No | 0.116 | D | E |
| 3 | S | — | Yes | 0.059 | B | A |
| 4 | S | — | No | 0.100 | D | E |
| 5 | P | 1.5 | No | 0.086 | D | D |
| 6 | P | 3.5 | No | 0.068 | B | A |
| 7 | P | 3.5 | Yes | 0.046 | A | A |
| 8 | P | 9 | No | 0.044 | A | A |
| 9 | S | 1 | No | 0.070 | B | B |
| 10 | S | 1.5 | No | 0.062 | B | A |
| 11 | S | 1.5 | Yes | 0.042 | A | A |
| 12 | S | 3 | No | 0.045 | A | A |
| 13 | S | 5 | No | 0.033 | A | A |
| 14 | S | 7 | No | 0.029 | A | A |
| 15 | S | 1.5 | No | 0.065 | B | A |

As is clear from the results shown in the table, the soap compositions prepared with the primary or secondary ester product without salting-out (No. 2 and No. 4) were inferior in color and odor in comparison with the conventional soap composition (No. 1) prepared with the primary ester product with salting-out. When the step of salting-out was included in the soap making process with the secondary ester product (No. 3), the result in the color of the soap composition was no more than a slight improvement. In the cases where the adsorption decolorization was undertaken with the primary ester product (No. 5 to No. 8), an amount of 3.5 to 9% by weight of the adsorbent was required when soap compositions apparently better in color and odor than the conventional one were obtained without salting-out. On the contrary, soap compositions of clearly better quality in color and odor were obtained with only 1 to 3% by weight of the adsorbent when the soap composition was prepared with the ester product purified according to the inventive method even without salting-out (No. 9 to No. 14). That is, the amount of the adsorbent could be reduced to about one third of the amount in the soap making with the primary ester product. The results of experiments No. 13 and No. 14 indicate that further increase of the amount of the adsorbent was beneficial in further decreasing the yellowness of the soap composition.

In experiment No. 15, the starting fatty acid glyceride was a 5:5 by weight mixture of beef tallow and coconut oil instead of 8:2 in the other experiments. The results of Experiment No. 15 were almost identical with those in No. 10 carried out otherwise with the same conditions indicating that the effectiveness of the inventive method is little affected by the composition of the starting fatty acid glycerides.

EXAMPLE 2

(Experiments No. 16 to No. 20)

Five kinds of soap compositions were prepared with the secondary ester product using 2% by weight of an adsorbent, in which the weight ratio of the activated clay to the active carbon was varied as indicated in Table 2 below with an object to determine the optimum proportion of them, the other conditions being the same as in the preceding Experiments. No salting-out was undertaken in all of the experiments. The soap compositions were evaluated for the color and odor. The results are given in Table 2.

TABLE 2

| Experiment No. | Activated clay:active carbon, weight ratio | Color of Soap | | Odor, organoleptic test |
|---|---|---|---|---|
| | | Yellowness | Organoleptic test | |
| 16 | 10:0 | 0.071 | B | A |
| 17 | 9:1 | 0.055 | B to A | A |
| 18 | 6:4 | 0.056 | B to A | A |
| 19 | 2:8 | 0.070 | B | A |
| 20 | 0:10 | 0.077 | C | B |

As is clear from the results in Table 2, omission of the activated clay (No. 20) resulted in the largest value of the yellowness and less preferable odor whereas satisfactory results were obtained when the activated clay was used either alone (No. 16) or as a combination with the active carbon (No. 17 to No. 19) with the best results obtained in No. 17 and No. 18 in which the weight ratio was 9:1 or 6:4, respectively.

EXAMPLE 3

(Experiments No. 21 to No. 31)

Eleven kinds of soap compositions were prepared substantially in the same manner as described in Example 1 with the secondary ester product except that the temperature and the time in the adsorption decolorization were varied as indicated in Table 3 below with an object to examine the effects of these parameters. The amount of the adsorbent, which was a 9:1 by weight mixture of the activated clay and the active carbon, was 2% by weight. No salting-out was undertaken in all of the experiments. In Experiments No. 21 to No. 26, the temperature in the adsorption decolorization was varied from 40° C. to 120° C. with the time being kept constant at 30 minutes in all of the experiments. The results indicate that the preferable temperature range is from 50° C. (No. 22) to 110° C. (No. 25) in respect of the reduced yellowness while the results at 40° C. (No. 21) and at 120° C. (No. 26) were less satisfactory. In particular, the most satisfactory results were obtained at 60° C. (No. 23) and at 100° C. (No. 24).

Experiments No. 27 to No. 31 were carried out by varying the time of agitation for the adsorption decolorization with the temperature always being kept at 80° C. As is shown in the table, excessive extension of the time to 120 minutes (No. 31) was undesirable due to the increased yellowness and satisfactory results were obtained with the agitation time in the range from 5 minutes (No. 27) to 90 minutes (No. 30), the best results being obtained with 10 minutes (No. 28) to 60 minutes (No. 29) of agitation.

TABLE 3

| Experiment No. | Decolorization by adsorption | | Color of soap | | Odor, organoleptic test |
|---|---|---|---|---|---|
| | Temperature, °C. | Time, minutes | Yellowness | Organoleptic test | |
| 21 | 40 | 30 | 0.078 | C | C |
| 22 | 50 | 30 | 0.068 | B | A |
| 23 | 60 | 30 | 0.056 | B to A | A |
| 24 | 100 | 30 | 0.057 | B to A | A |
| 25 | 110 | 30 | 0.069 | B | B |
| 26 | 120 | 30 | 0.081 | D | D |
| 27 | 80 | 5 | 0.068 | B | A |
| 28 | 80 | 10 | 0.056 | B to A | A |
| 29 | 80 | 60 | 0.054 | B to A | A |
| 30 | 80 | 90 | 0.062 | B | A |
| 31 | 80 | 120 | 0.075 | C | C |

EXAMPLE 4

(Experiments No. 32 to No. 35)

Stability tests of 4 soap compositions were undertaken in respects of the light resistance and heat resistance. The soap compositions tested were prepared by repeating the procedures in Experiments No. 1, No. 10, No. 11 and No. 12 in Example 1 with the same starting ester products as in the respective Experiments. In this stability test, no perfume was added to the soap composition to avoid the strong influence of the perfume on the stability of soap compositions and to obtain results of the stability with the soap base per se. Table 4 below summarizes the results of the yellowness of the soap compositions as prepared, after 10 days of the light resistance test and after 14 days of the heat resistance test.

As is shown in the table, the yellowness always decreased in the exposure to light due to the bleaching effect by the ultraviolet light with the order of the values unchanged among 4 samples even though the differences between the values were decreased. On the other hand, the yellowness of the soap compositions increased by the heat resistance test of 14 days with about the same increments of 0.038-0.039 keeping the superiority of the soap compositions prepared by the inventive method over the conventional. The conclusion of the stability test is that the stability of the soap compositions prepared by the inventive method is approximately identical with conventional ones in the resistance against both light and heat.

TABLE 4

| Experiment No. | 32 | 33 | 34 | 35 |
|---|---|---|---|---|
| Soap making conditions, the same as in Experiment No. | 1 | 10 | 11 | 12 |
| as prepared | 0.064 | 0.061 | 0.045 | 0.047 |
| after 10 days of | | | | |

TABLE 4-continued

| Experiment No. | | 32 | 33 | 34 | 35 |
|---|---|---|---|---|---|
| Yellow-ness | light resistance test | 0.044 | 0.043 | 0.032 | 0.032 |
| | after 14 days of heat resistance test | 0.102 | 0.100 | 0.084 | 0.085 |

What is claimed is:

1. A method for the preparation of a high-quality lower alkyl ester of a fatty acid which comprises the steps of
   (a) esterifying a fatty acid glyceride by a first alcoholysis reaction with a lower alcohol in the presence of an alkali catalyst to form a first crude esterification product and glycerine,
   (b) separating the glycerine from the first crude esterification product,
   (c) esterifying the first crude esterification product by a second alcoholysis reaction with the lower alcohol in the presence of an alkali catalyst to form a second esterification product containing the unreacted lower alcohol and glycerine as dissolved or dispersed therein,
   (d) admixing the second crude esterification product with water in an amount from 30% to 150% by weight based on the amount of the lower alcohol contained in the second crude esterification product,
   (e) subjecting the second crude esterification product admixed with water to phase separation into the aqueous layer and layer of the lower alkyl ester of fatty acid,
   (f) stripping the lower alkyl ester of fatty acid of the water and unreacted lower alcohol contained therein,
   (g) admixing the thus stripped lower alkyl ester of fatty acid with from 1 to 10% by weight of an adsorbent to effect decolorization, and
   (h) removing the adsorbent from the thus decolorized lower alkyl ester of fatty acid.

2. The method as claimed in claim 1 wherein the adsorbent is an activated clay.

3. The method as claimed in claim 1 wherein the adsorbent is a mixture of an activated clay and an active carbon in a weight ratio from 9:1 to 2.8.

4. The method as claimed in claim 2 or claim 3 wherein the amount of the adsorbent is in the range from 1.5 to 5% by weight based on the amount of the lower alkyl ester of fatty acid.

5. The method as claimed in claim 2 or claim 3 wherein the admixing of the lower alkyl ester of fatty acid with the adsorbent is carried out at about 50° to 110° C. for about 5 to 90 minutes with agitation.

* * * * *